United States Patent [19]
Simon et al.

[11] Patent Number: 5,354,308
[45] Date of Patent: Oct. 11, 1994

[54] METAL WIRE STENT

[75] Inventors: Morris Simon, Boston; Dmitry J. Rabkin, Brookline; Stephen Kleshinski, Scituate, all of Mass.

[73] Assignee: Beth Israel Hospital Association, Boston, Mass.

[21] Appl. No.: 878,184

[22] Filed: May 1, 1992

[51] Int. Cl.⁵ .............................................. A61M 29/00
[52] U.S. Cl. ..................................... 606/198; 623/12; 623/1
[58] Field of Search ...................... 623/1, 12; 606/191, 606/192, 198

[56] References Cited

U.S. PATENT DOCUMENTS

| | | | |
|---|---|---|---|
| 4,425,908 | 1/1984 | Simon | 128/1 R |
| 4,512,338 | 4/1985 | Balko et al. | 604/191 |
| 4,553,545 | 11/1985 | Maass et al. | 128/341 |
| 4,580,568 | 4/1986 | Gianturco | 604/96 |
| 4,655,771 | 4/1987 | Wallsten | 623/1 |
| 4,733,665 | 3/1988 | Palmaz | 128/343 |
| 4,739,762 | 4/1988 | Palmaz | 623/1 |
| 4,768,507 | 9/1988 | Fischell et al. | 128/303 R |
| 4,830,003 | 5/1989 | Wolff et al. | 128/343 |
| 4,886,062 | 12/1989 | Wiktor | 128/343 |
| 4,969,458 | 11/1990 | Wiktor | 606/194 |
| 5,034,001 | 7/1991 | Garrison et al. | 604/53 |
| 5,217,483 | 6/1993 | Tower | 606/198 |

FOREIGN PATENT DOCUMENTS 1205743  9/1970  United Kingdom ............... 608/198

Primary Examiner—Jerome L. Kruter
Attorney, Agent, or Firm—Lorusso & Loud

[57] ABSTRACT

A stent comprising a wire skeletal frame, the frame being adapted to assume a first condition in which the frame is relatively rigid and substantially tubular in configuration and a second condition in which the frame is flexible, of reduced stress, and collapsible, such that in the second condition walls of the frame are adapted to be positioned against each other to form a stent diameter substantially equal to the combined thickness of the frame walls in abutting engagement with each other, the frame in its second condition being substantially devoid of bias therein urging the frame to assume the first configuration.

11 Claims, 5 Drawing Sheets

METAL WIRE STENT

BACKGROUND OF THE INVENTION

1. Field of the Invention

This invention relates to stents and is directed more particularly to a self-expanding, generally cylindrical stent which is repositionable after being set in place.

2. Brief Description of the Prior Art

Self-expanding stents are generally known in the art. U.S. Pat. No. 4,580,568, issued Apr. 8, 1986, to Cesare Gianturco, discloses an endovascular stent formed of stainless steel wire. The stent is compressed into a reduced size having an outer diameter substantially smaller than the stent in its expanded shape. The stent is held in its compressed state during its passage through a small bore catheter until delivered into a vascular system passageway, whereupon the stress in the stent causes the stent to expand in the larger bore vascular passageway to hold open the passageway. When the stent is compressed, the bends in the wire, which is of a zig-zag configuration, store stress, and the stent is expandable by the release of the stress stored in the bends. Once set in place, the radial extremities of the stent bear against the inside walls of the passageway. There is no ready means by which the stent may be again compressed, or softened, so that the stent may be repositioned.

It would be beneficial to the medical arts to have available a stent adapted for compression into a small size to facilitate introduction into a vascular passageway, and adapted for self-expansion in the vascular passageway to hold open the passageway, and also adapted to be softened and/or contracted to permit repositioning of the stent.

SUMMARY OF THE INVENTION

It is, therefore, an object of the invention to provide a stent adapted to assume a first configuration in which the stent is expanded, capable of exercising considerable stress if confined, as by a vessel wall, and substantially tubular in configuration for holding open a vascular passageway, and a second configuration in which the stent is flexible, in a reduced stress state, and adapted to be compressed into a small enough size to fit within the small bore of a delivery catheter.

A further object of the invention is to provide such a stent which is adapted to change from the first condition of relative rigidity to the second condition of flexibility and reduced stress, by exposure to a preselected transition temperature, such that the stent may be relaxed in place in a vascular passageway by cooling to facilitate repositioning thereof without damage to walls of the passageway.

A still further object of the invention is to provide such a stent laminated within an elastomeric sleeve, the sleeve being expandable to conform to the stent's first, i.e. rigid, condition and having therein a bias towards assuming a smaller size, such that upon the stent's assuming the second, i.e. flexible, condition, the sleeve operates to compress the stent to a size less than its expanded size.

With the above and other objects in view, as will hereinafter appear, a feature of the present invention is the provision of a stent comprising a wire skeletal frame, the frame being adapted to assume a first condition in which the frame is expanded, rigid, and substantially tubular in configuration, the frame being further adapted to assume a second condition in which the frame is flexible, of reduced stress and collapsible, such that in the second condition walls of the frame are adapted to be positioned in their collapsed disposition, and further adapted to be positioned against each other to form a stent diameter substantially equal to the combined thickness of the frame walls in abutting engagement with each other, and further adapted to be positioned between the expanded disposition and the walls abutting engagement disposition, the frame in the second condition being substantially devoid of bias present therein urging the frame to assume the first configuration.

In accordance with a further feature of the invention, there is provided a stent, as described immediately above, and further comprising an elastomeric sleeve disposed on the stent and expandable therewith to conform to the stent's expanded condition, the sleeve having therein a bias exerting a compressive force on the stent, such that upon cooling of the stent below a selected transition temperature, the sleeve urges the flexible and low stress stent to a third configuration smaller than the stent in its expanded condition and larger than the stent in its walls abutting configuration.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

DESCRIPTION OF THE PREFERRED EMBODIMENT

Figure 1:
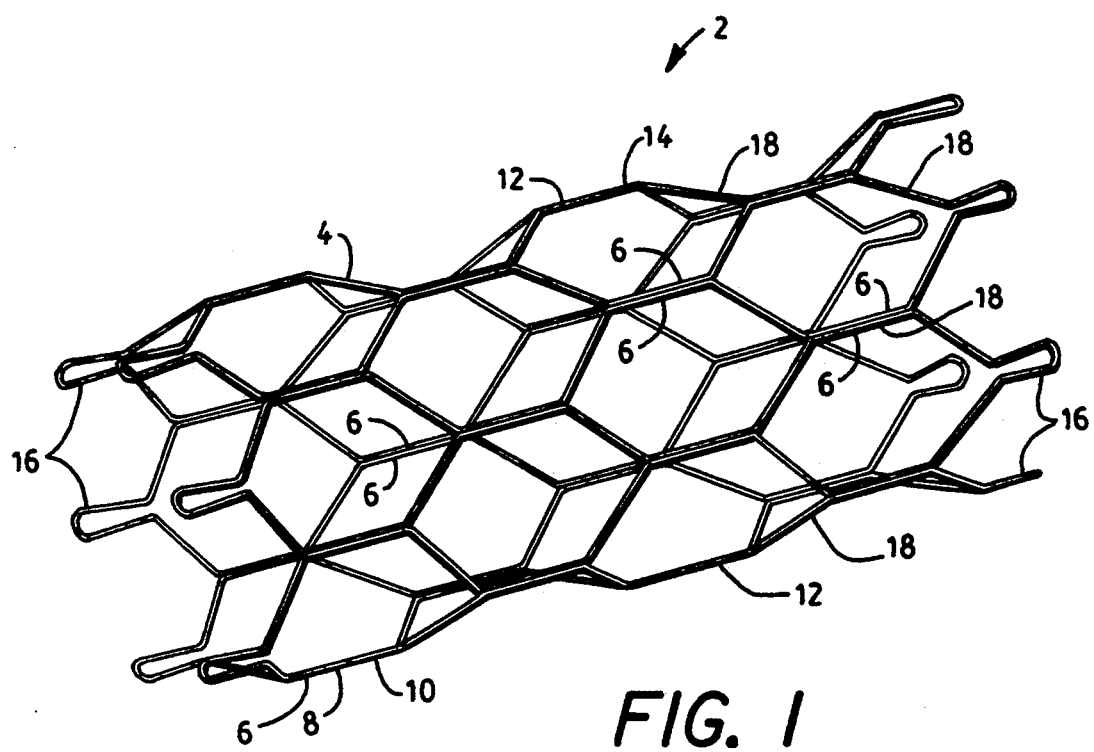
FIG. 1 is a perspective view of one form of stent illustrative of an embodiment of the invention.
Figure 2:
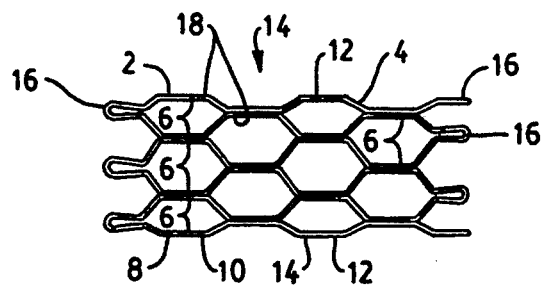
FIG. 2 is a side elevational view thereof.

Referring to FIGS. 1 and 2, it will be seen that an illustrative stent includes a skeletal frame 2, preferably formed from a single wire 4. The wire 4 includes a plurality of abutting straight portions 6 which are joined to each other, as by welding.

In FIGS. 1 and 2, the illustrative stent is shown in a first condition in which the frame 2 is expanded, relatively rigid, and substantially tubular in configuration. Ends 8, 10 of the single wire 4 are disposed in one of the welded straight portions 6, such that there are no exposed wire free ends, disposed within or extending from the frame 2. The abutting and elongated straight portions 6 of the wire 4 facilitate the use of strong elongated welds to securely join the wire portions 6 together. The wire 4 preferably is round in cross-section. In the frame straight portions 6 the joined wire segments are disposed, relative to the tubular configuration of the frame, circumferentially thereof. The wire 4 abuts itself only at the straight portions 6 and does not cross itself at any point. Accordingly, the frame walls, that is, walls 12 of a tubular body portion 14 of the frame 2 have a thickness equal to the diameter of the wire 4.

Figure 3:
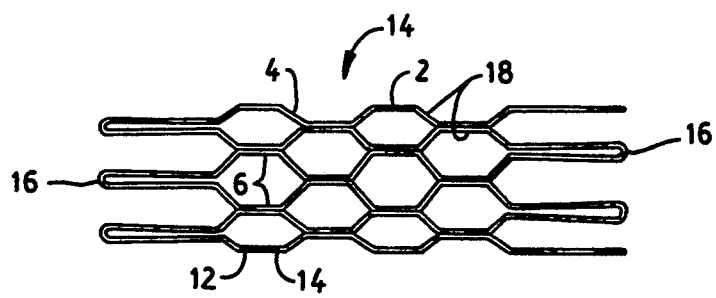
FIG. 3 is a side elevational view of an alternative embodiment thereof.

The stent includes the body portion 14 and finger portions 16 extending generally axially from one, or both, ends of the body portion. The fingers facilitate a gradual reduction in radially outwardly extending pressure exerted by the stent on the wall of a vascular passageway in which the stent is located. Such gradual reduction of pressure facilitates acceptance of the stent by the passageway and reduces deleterious reactions by the passageway wall to the presence of the stent. Referring to FIG. 3, it will be seen that the finger portion 16 may be extended further axially to lessen the probability of adverse reaction by the passageway wall to the pressure exerted against the wall by the stent frame 2.

Figure 4:
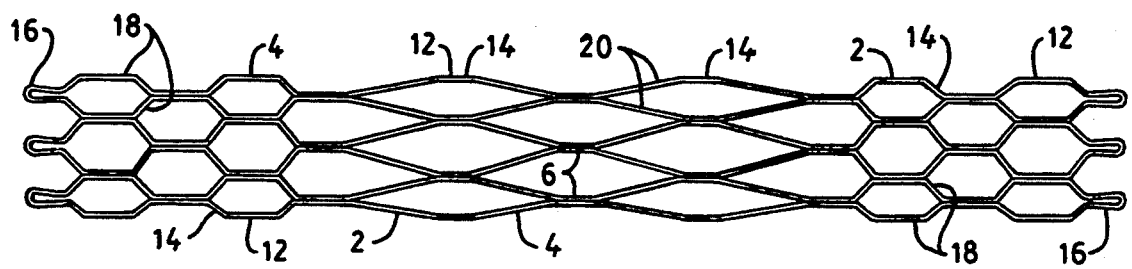
FIG. 4 is a side elevational view of a second alternative embodiment thereof.

The tubular body portion 14 comprises a mesh formed by the wire 4, the mesh comprising a plurality of interconnected cells 18 of a polygonal configuration when viewed in plan, providing straight sides to form the aforementioned straight portions 6. The polygonal cells 18 preferably are of a hexagonal configuration, which readily provides expansion and rigidity characteristics desirable in the structure and operation of the device. Preferably, the stent comprises six of the polygonal cells 18 circumferentially and an even number of the polygonal cells along its length, thereby facilitating formation of the stent by the single wire 4. The portion of the stent having the mesh construction exercises a substantially greater radial bias than do the finger portions 16. Thus, when it is desired to have more force near the ends of the stent than at its center, the embodiment shown in FIG. 4 may be used. Referring to FIG. 4, it will be seen that in this embodiment, the central portion of the tubular body portion 14 includes elongated cells 20 exercising less radial force than the cells 18.

The stent preferably is made of an alloy of nickel and titanium which provides the stent with a thermal memory. The unique characteristic of this alloy, known generally as "Nitinol", is its thermally triggered shape memory, which allows the stent constructed of the alloy to be cooled and thereby softened for loading into a catheter in a relatively compressed and elongated state, and regain the memoried shape when warmed to a selected temperature, such as human body temperature. The two interchangeable shapes are possible because of the two distinct micro-crystalline structures that are interchangeable with a small variation in temperature. The temperature at which the stent assumes its first configuration may be varied within wide limits by changing the composition of the alloy. Thus, while for human use the alloy may be focused on a temperature of 98.6° F. for assumption of the first condition, the alloy readily may be modified for use in animals with different body temperatures.

Figure 5:
FIG. 5 is a side elevational view of the stent shown in FIG. 1, but shown in a compressed condition.
Figure 7A:
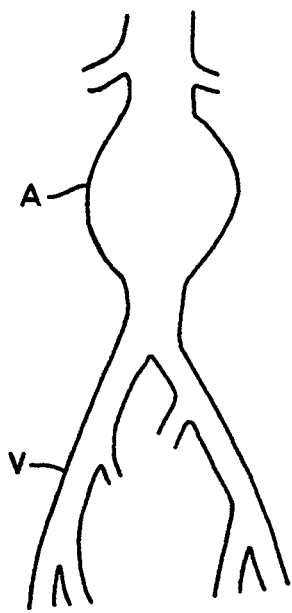
FIGS. 7A–7C are illustrative stylized diagrammatic views of one manner of use of the inventive devices of FIGS. 1–6, as in the treatment of an aneurysm of a large artery.
Figure 7B:
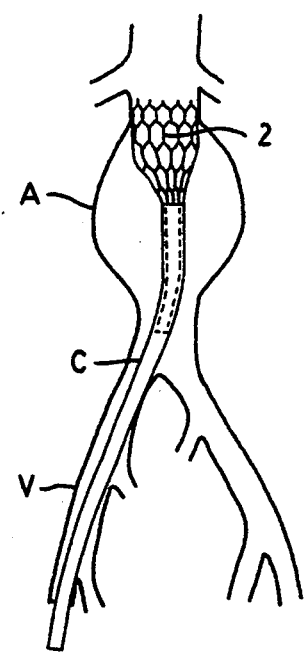

Accordingly, when the stents shown in FIGS. 1–4 are subjected to a temperature at or less than the transition temperature, the relatively rigid stent changes to a second condition in which it is flexible, of reduced stress and collapsible. The stent does not, of its own accord, collapse, or compress, but the stent does become quite pliable, collapsible and compressible. By mechanical means, the stent may be compressed to a point at which the walls 12 of the body portion 14 of the stent frame 2 are positioned against each other, to form a stent diameter substantially equal to the combined thickness of the frame walls in abutting engagement with each other. In FIG. 5, the stent is shown approaching, but not yet having reached such minimal stent diameter. In the compressed condition, the stent is readily contained by a catheter C (FIG. 7B).

Figure 6:
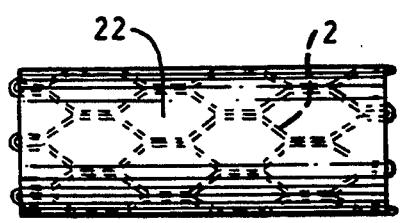
FIG. 6 is a side elevational view of the stent shown in FIGS. 1 and 2 with an elastomeric sleeve thereon.

In FIG. 6, there is shown an alternative embodiment having still further benefits. As noted above, in the second condition of the stent, the stent becomes flexible and compressible, but does not of its own accord compress. In the embodiment shown in FIG. 6, the stent body portion has disposed thereon an elastomeric sleeve 22. The sleeve 22 is expandable on the frame 2 as the frame expands to its enlarged configuration. However, as the sleeve expands, the sleeve exerts a compressive force on the frame. Upon cooling of the stent to or below the transition temperature, the stent becomes flexible and the compressive sleeve 22 urges the frame 2 to a third configuration of smaller diameter than the first configuration. Accordingly, upon cooling of the sleeved embodiment, the flexible frame automatically reduces in size, thereby rendering any repositioning of the stent, as by a grasping tool or other instrument, known in the art (not shown), a relatively simple matter. Again, upon removal of the cooling medium, the sleeved stent returns to its expanded condition.

The sleeved stent has an added benefit in that while an unsleeved stent will suffice in many instances, there are occasions when the affected passageway wall is in such a weakened condition that the provision of a new wall, or a graft, is required. The sleeved stent is essentially a graft and operates to provide a new passageway wall when required.

In operation, the stent, sleeved or unsleeved, is carried through an affected vascular passageway V (FIG. 7A) by the catheter C (FIG. 7B), which is of a thermally insulative material. At room temperature, and while cooled by infusion of a cool solution within the catheter, the stent remains in the second condition, flexible and of low stress. Being of low stress, the stent exercises negligible radial force against the inside wall of the catheter and is easily moved through the catheter at the appropriate time.

Figure 7C:
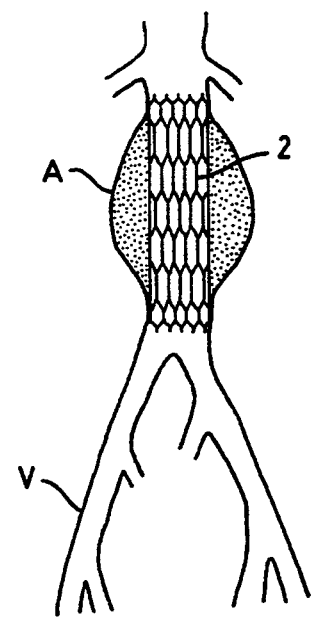

As the catheter enters the passageway V, the thermal insulative properties of the catheter and the flow of cool solution maintain the stent at less than body temperature. When the distal end of the catheter is properly disposed, as for example, in the vicinity of an aneurysm A (FIG. 7B), the stent is moved out of the end of the catheter C. As the stent contacts blood flow, and is subjected to body temperature, the exposed stent immediately and rapidly assumes its first condition, expanding against the walls of the passageway. Upon total ejection of the stent, the catheter is removed, leaving the stent in place to act as an internal wall graft (FIG. 7C).

Figure 8A:
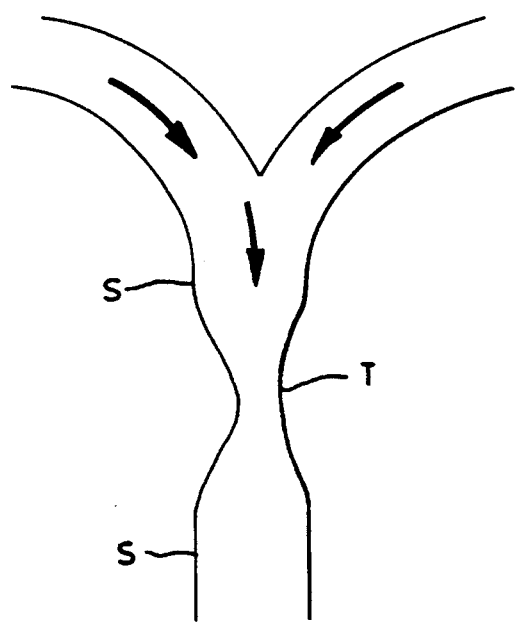
FIGS. 8A–8C are stylized diagrammatic views illustrative of another manner of use of the inventive device of FIGS. 1–6, as in the treatment of compression or narrowing of a vessel.
Figure 8B:
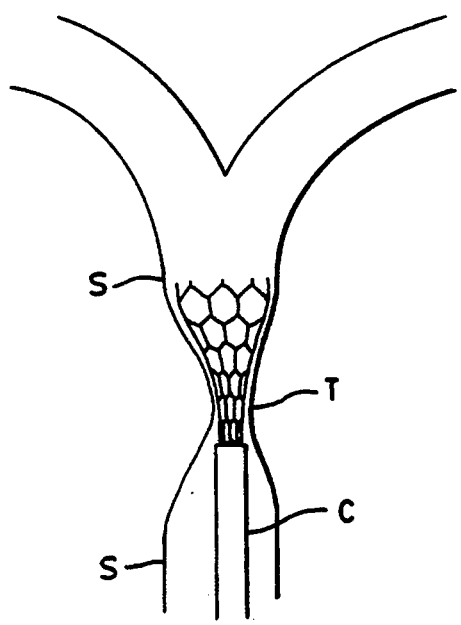
Figure 8C:
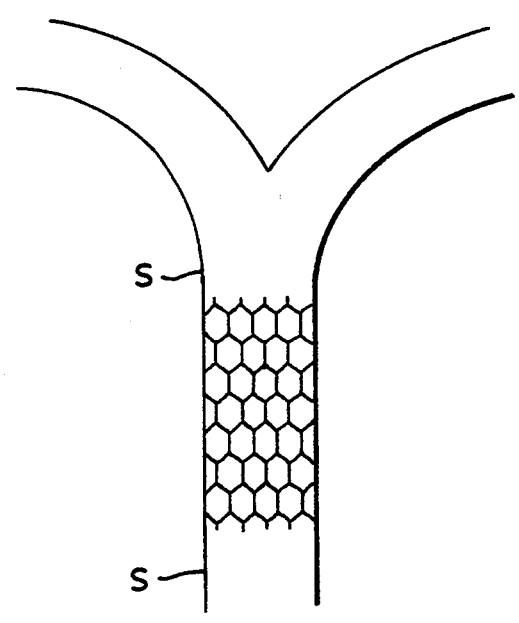

Referring to FIGS. 8A–8C, it will be seen that in treatment of compression of a large vessel, such as a superior vene cava S, the catheter C (FIG. 8B) is moved through the vessel S to a point adjacent a stricture T. The stent 2 is moved from the catheter C, while the catheter is withdrawn, to place the emerging stent within the vessel and in the area of the stricture ( FIG. 8B). As the stent emerges from the catheter, the stent, as it is exposed to the blood stream, assumes its first condition. Upon total removal of the stent from the catheter, the stent in its entirety is expanded against the wall of the vessel (FIG. 8C) to maintain the vessel in a free-flowing configuration.

The ratio of expanded stent diameter to compressed stent diameter can be controlled within limits by selection of wire diameter. The diameter of the expanded stent generally is on the order of 6 to 10 times the diameter of the compressed stent. In general, the greater the diameter of the wire 4, the less the ratio of the stent collapsed/expanded diameter. By selection of wire diameter, it is possible to vary the radial force which the expanded stent will exert on the interior walls of the passageway in which the stent is set.

Figure 9A:
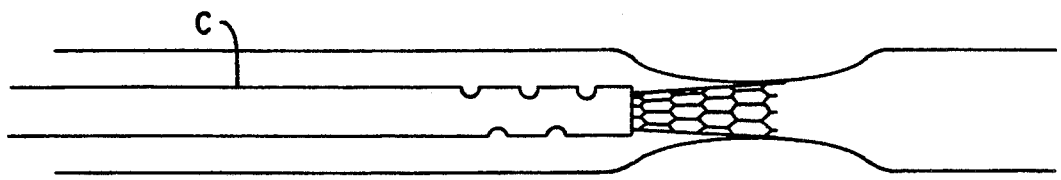
FIGS. 9A–9E are stylized diagrammatic views illustrative of a manner of repositioning the inventive device of FIGS. 1–6.
Figure 9B:
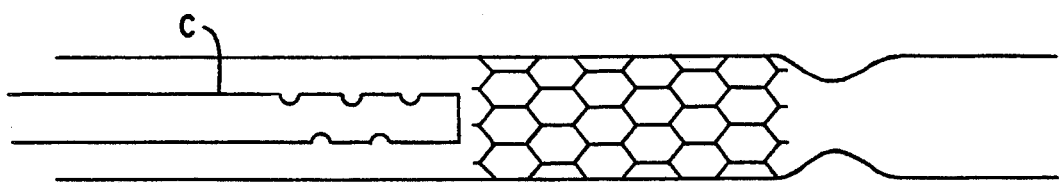
Figure 9C:
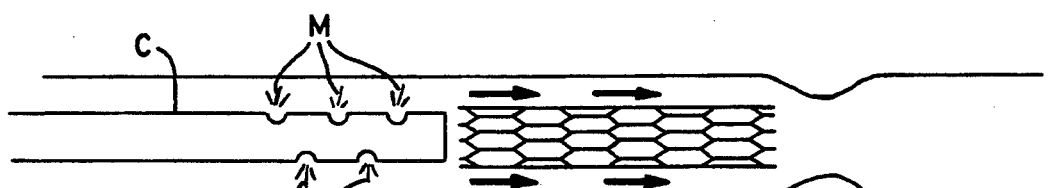
Figure 9D:
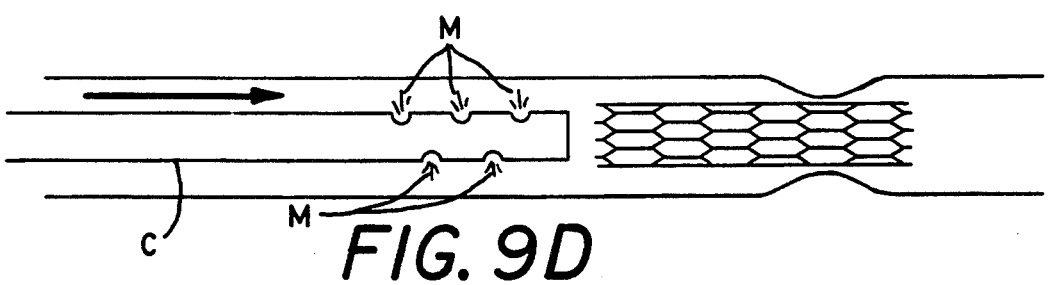
Figure 9E:
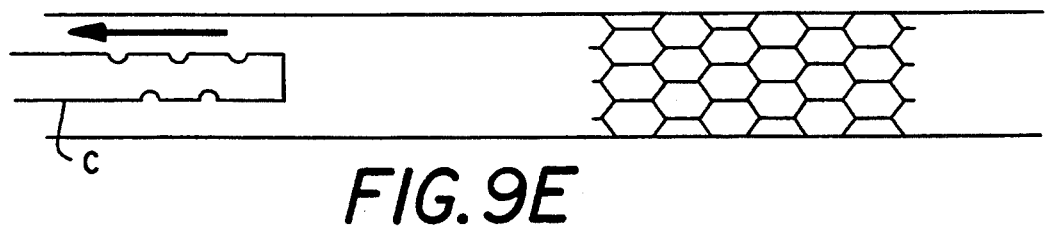

It is sometimes the case that once the stent is in place and in part expanded, it is recognized that the stent is somewhat off target (FIGS. 9A and 9B) and requires repositioning. To reposition the stent of the present invention, the operator introduces into the passageway a cool medium M (FIGS. 9C and 9D), such as a saline solution, having a temperature at or less than the transition temperature. When the cool solution encounters the stent, the stent immediately turns flexible and surrenders radial force against the passageway walls. In such relaxed state, the stent, which has no free wire ends, is easily slid into the proper position by manipulation of the catheter C (FIG. 9D), whereupon the flow of cool solution is stopped and the stent, upon returning to a body temperature, reassumes its expanded condition in the passageway (FIG. 9E). The cathether C is then withdrawn from the stent and from the passageway.

Thus, there is provided a stent which may be alloyed to have a selected temperature at which the stent assumes its first condition and a selected transition temperature, at which the stent assumes its second condition, and which includes a wire frame, wherein the diameter of the wire is selectable to provide a selected degree of expansion force. The stent is compressible to less than a catheter-size diameter to facilitate delivery of the stent to a location within a body passageway by a catheter. The stent may be sleeved or unsleeved. The stent is self-expanding upon delivery from the catheter and introduction to a body temperature, to provide an internal graft or hold open a passageway. Even after such positioning and expansion, the stent is rendered flexible and readily repositionable merely by the flow of a cool medium through the stent. And, finally, by termination of the flow of cool fluid, the stent automatically reassumes its passageway supporting rigid condition. Any required subsequent repositioning can be accomplished in the same manner.

It is to be understood that the present invention is by no means limited to the particular constructions herein disclosed and/or shown in the drawings, but also comprises any modifications or equivalents within the scope of the claims. For example, while the use of the stent has been illustrated in connection with the vascular system, it will be apparent to those skilled in the art that the stent herein shown and described finds equal utility in other bodily passageways.

Having thus described our invention, what we claim as new and desire to secure by Letters Patent of the United States is:

1. A stent comprising a wire skeletal frame, said frame being adapted to assume a first condition in which said frame is expanded, relatively rigid, and substantially tubular in configuration, and being further adapted to assume a second condition in which said frame is flexible, of reduced stress, and collapsible, said wire frame comprised of a metallic compound of nickel and titanium, said compound in said second condition indefinitely retaining said flexibility and said reduced stress and retaining memory of said first condition, said wire frame upon heating to a selected body temperature, assuming said first condition in which said frame is greatly expanded relative to said second condition and assuming said rigidity, such that in said second condition walls of said frame are adapted to be positioned in their collapsed disposition, and further adapted to be dispositioned against each other to form a stent diameter substantially equal to the combined thickness of the frame walls in abutting engagement with each other, and further adapted to be configured between said expanded disposition and said walls abutting disposition, said frame in said second condition being substantially devoid of bias present therein urging said frame to assume said first configuration, said skeletal frame comprising only a single wire round in cross-section, said frame including straight axially-extending portions of said wire joined together along the lengths of said straight axially-extending portions and circumferentially side by side, wherein in said substantially tubular configuration said frame includes a substantially tubular body portion and finger portions extending from an end of said tubular body portion, said finger portions extending axially of said tubular body portion and comprising endless looped portions of said single wire.

2. The stent in accordance with claim 1 wherein first and second ends of said single wire are disposed in one of said joined straight portions of said wire, whereby said frame is devoid of exposed free ends of said wire.

3. The stent in accordance with claim 1 wherein said selected body temperature is normal human body temperature, whereby said frame is adapted to assume said first configuration automatically upon exposure to a human body blood stream.

4. The stent in accordance with claim 1 wherein said frame tubular body portion comprises a mesh formed of said wire, said mesh comprising a plurality of cells which in plan view are of polygonal configuration, each of said fingers extending from one of said cells at an end of said tubular body portion.

5. The stent in accordance with claim 1 wherein said polygonal configurations are hexagonal configurations.

6. The stent in accordance with claim 1 wherein the diameter of said frame in said first configuration is about 6 to 10 times the diameter of said frame in said second configuration.

7. The stent in accordance with claim 1 wherein said single wire abuts itself only at said straight portions.

8. The stent in accordance with claim 1 wherein the thickness of said tubular body portion wall is of a thickness equal to the diameter of said wire.

9. A stent comprising a wire skeletal frame, said frame being adapted to assume a first condition in which said frame is expanded, relatively rigid, and substantially tubular in configuration, and being further adapted to assume a second condition in which said frame is flexible, of reduced stress, and collapsible, said wire frame comprised of a metallic compound of nickel and titanium, said compound in said second condition indefinitely retaining said flexibility and said reduced stress and retaining memory of said first condition, said wire frame upon heating to a selected body temperature, assuming said first condition in which said frame is greatly expanded relative to said second condition and assuming said rigidity, such that in said second condition walls of said frame are adapted to be positioned in their collapsed disposition, and further adapted to be positioned against each other to form a stent diameter substantially equal to the combined thickness of the frame walls in abutting engagement with each other, and further adapted to be configured between said expanded disposition and said walls abutting disposition, said frame in said second condition being substantially devoid of bias present therein urging said frame to assume said first configuration, said skeletal frame comprising only a single wire round in cross-section, said frame including straight axially-extending portions of said wire joined together along the lengths of said straight axially-extending portions and circumferentially side by side, said stent further comprising an elastomeric sleeve disposed about said frame, said sleeve being expandable on said frame as said frame expands to said first configuration, said sleeve in said expanded condition exercising a compressive force on said frame, whereby upon cooling of said frame to or below said transition temperature, said sleeve urges said flexible frame to a third configuration of smaller diameter than said first configuration, and whereby upon subsequent heating of said frame to or above said selected body temperature, said frame returns to said first condition and said sleeve expands accordingly to conform to said expanded frame.

10. A stent comprising a wire skeletal frame of generally tubular configuration, said skeletal frame comprising only a single wire, said wire being round in cross-section, said frame including straight axially-extending portions of said wire joined together along the lengths of said straight axially-extending portions, and disposed side by side defining a circumference of said stent, wherein said frame includes a substantially tubular body portion and finger portions extending from an end of said body portion, said finger portions extending axially of said body portion and comprising endless looped portions of said single wire.

11. The stent in accordance with claim 10 wherein said body portion comprises a mesh formed of said wire, said mesh comprising a plurality of polygonal cells, each of said fingers extending from one of said cells at an end of said body portion.

* * * * *